US007789852B2

(12) United States Patent
Yoshikawa et al.

(10) Patent No.: US 7,789,852 B2
(45) Date of Patent: Sep. 7, 2010

(54) MEDICAL LIQUID CONTAINER AND PREPARATION-CONTAINING MEDICAL LIQUID CONTAINER

(75) Inventors: Katsuyuki Yoshikawa, Ichihara (JP); Manabu Nakamura, Yokohama (JP)

(73) Assignee: Hosokawa Yoko Co., Ltd., Tokyo (JP)

( * ) Notice: Subject to any disclaimer, the term of this patent is extended or adjusted under 35 U.S.C. 154(b) by 407 days.

(21) Appl. No.: 11/791,372

(22) PCT Filed: Nov. 25, 2005

(86) PCT No.: PCT/JP2005/022125

§ 371 (c)(1),
(2), (4) Date: May 23, 2007

(87) PCT Pub. No.: WO2006/057442

PCT Pub. Date: Jun. 1, 2006

(65) Prior Publication Data

US 2007/0299391 A1 Dec. 27, 2007

(30) Foreign Application Priority Data

Nov. 26, 2004 (JP) ............................. 2004-342695
Nov. 11, 2005 (JP) ............................. 2005-327087

(51) Int. Cl.
*A61M 5/14* (2006.01)

(52) U.S. Cl. .......................................... 604/80; 604/86

(58) Field of Classification Search ................... 604/82, 604/80, 81, 83–92; 383/48–50
See application file for complete search history.

(56) References Cited

U.S. PATENT DOCUMENTS 4,526,176 A * 7/1985 Bremer et al. .............. 600/392
4,602,910 A * 7/1986 Larkin ......................... 604/87
5,423,421 A * 6/1995 Inoue et al. ................. 206/219
5,944,709 A * 8/1999 Barney et al. ............... 604/410

(Continued)

FOREIGN PATENT DOCUMENTS

CN 1531917 A 9/2004

(Continued)

OTHER PUBLICATIONS

Patent Abstracts of Japan, vol. 2003, No. 12, Dec. 5, 2003 & JP 2004-313760 A (Nipro Corp), Nov. 11, 2004 Abstract, Figure 2.

*Primary Examiner*—Nicholas D Lucchesi
*Assistant Examiner*—Gerald Landry, II
(74) *Attorney, Agent, or Firm*—Sughrue Mion, PLLC

(57) ABSTRACT

To provide a medical liquid container which is free from sealing failure in the seal portion at the peripheral edge of the liquid medicament-housing chamber and also free from deterioration of a medicament housed in a small amount; and a preparation-containing medical liquid container. A secondary liquid medicament-housing chamber 12 is connected to one end of a primary liquid medicament-housing chamber 11. This secondary liquid medicament-housing chamber 12 is unseparably fixed to the primary liquid medicament-housing chamber 11 at a connection part 14. The secondary liquid medicament-housing chamber 12 has a bulge part 15 bulged such that the internal medicament-housing space before housing a second medicament is larger than the volume of the housed second medicament.

10 Claims, 7 Drawing Sheets

U.S. PATENT DOCUMENTS

| | | | | |
|---|---|---|---|---|
| 6,083,584 | A * | 7/2000 | Smith et al. | 428/35.2 |
| 6,247,586 | B1 | 6/2001 | Herzog et al. | |
| 6,484,874 | B1 | 11/2002 | Kageyama et al. | |
| 7,207,970 | B2 * | 4/2007 | Hasegawa | 604/90 |
| 7,243,787 | B2 * | 7/2007 | Iwasa et al. | 206/219 |
| 2005/0075613 | A1 * | 4/2005 | Hasegawa | 604/257 |
| 2005/0221034 | A1 | 10/2005 | Iwasaki et al. | |
| 2006/0072858 | A1 * | 4/2006 | Kurosawa et al. | 383/44 |
| 2009/0310890 | A1 * | 12/2009 | Suzuki et al. | 383/38 |

FOREIGN PATENT DOCUMENTS

| | | | |
|---|---|---|---|
| JP | 2000-5275 | A | 1/2000 |
| JP | 2001-87350 | A | 4/2001 |
| JP | 2002-165864 | A | 6/2002 |
| JP | 200305531 | | 1/2003 |
| JP | 2003-62038 | A | 3/2003 |
| JP | 2003-159309 | A | 6/2003 |
| JP | 2004-476 | A | 1/2004 |
| JP | 200412926 | | 1/2004 |
| JP | 2004-313760 | A | 11/2004 |
| WO | WO 2004/099028 | A1 | 11/2004 |

* cited by examiner

MEDICAL LIQUID CONTAINER AND PREPARATION-CONTAINING MEDICAL LIQUID CONTAINER

CROSS-REFERENCE TO RELATED APPLICATIONS

This application claims the benefit pursuant to 35 U.S.C. §119 (e)(1) of U.S. Provisional Application No. 60/632,951 filed on Dec. 6, 2004, and priority is claimed on Japanese Patent Application No. 2004-342695, filed Nov. 26, 2004, and Japanese Patent Application No. 2005-327087, filed Nov. 11, 2005, the contents of which are incorporated herein by reference.

TECHNICAL FIELD

The present invention relates to a medical liquid container for housing a medical preparation such as drip-feed solution, and a preparation-containing medical liquid container obtained by housing a medical preparation in the medical liquid container.

BACKGROUND ART

Some medicaments are used alone but in many cases, a plurality of medicaments are administered in combination to a patient. Particularly, in the case of a liquid injection administered by transfusion, it is often performed to prepare the injection by mixing medicaments or co-inject a slight amount of a secondary medicament into the primary medicament. Such an operation must be sterilely performed. This sterile dispensing operation is cumbersome and a danger of causing a dispensing failure is noted. Efforts have been heretofore made to improve this dispensing operation from the aspect of medical liquid container and thereby elevate safety and efficiency.

As for the container used in the medical field, a liquid medicament container where a plurality of contents are housed in a plurality of chambers partitioned in one container and although respective contents are not mixed before use, the contents can be easily mixed on use is known. For example, with respect to the liquid medicament container of preparing a transfusion preparation by mixing multiple species of medicaments immediately before transfusing the transfusion preparation, a liquid medicament container with multiple chambers is known, where a seal part produced by heat-melt bonding inner wall faces of a bag-shaped container formed of a synthetic resin-made film is used as a partition and medicaments are housed in a plurality of chambers partitioned by the seal part within the bag-shaped container. In a known constitution of such a liquid medicament container with multiple chambers, a rupturable liquidtight plug member is interposed in a part of the partition formed by the seal part and respective chambers are allowed to communicate by rupturing the liquidtight plug so that medicaments divided and housed in a plurality of chambers can be mixed.

Also, a container using a peelable weak seal for a part or the entirety of the partition formed by a seal part is known, where respective chambers are allowed to communicate by stripping the peelable weak seal by means of pressing or the like and thereby liquid medicaments divided and housed in multiple chambers can be mixed. These containers have a constitution such that at the time of performing transfusion by using the medicaments housed, the partition dividing respective chambers is caused to allow for communication and create one continuous chamber inside the container.

Out of these liquid medicament containers each with multiple chambers, in a medical liquid container having a primary medicament-housing chamber and a secondary medicament-housing chamber for housing a small amount of a medicament as in the case where the inner content largely differs among liquid medicaments housed in respective liquid medicament-housing chambers, when the communicatable partitioning means used therefor is a weak seal part conventionally employed for a medical liquid container with two chambers, the production is more facilitated than in the case of using another partition member and since communication can be attained by pressing one chamber to increase the inner pressure of the liquid medicament, the liquid medicaments can be easily mixed on use. Furthermore, the container comprising a sheet material has high flexibility, requires no air-passing needle, is excellent in hygiene, safety and workability such that the liquid discharge rate is kept constant throughout transfusion, realizes a small volume when wasted and ensures volume decrease at the disposal and therefore, this container is preferred as compared with conventional vials or medical liquid containers in which the entire is produced by blow molding.

In the medicament-housing chambers partitioned by using a sheet material and forming a seal part, since the sheet material is flat, the medicament-housing chamber before charging a medicament is naturally in a state having a volume of nearly 0. The medical container comprising a sheet material takes an inflated shape for the first time when a medicament is housed therein and the sheet material is deformed under a pressure generated due to self-weight of the medicament. Particularly, in the case of a relatively small-content secondary medicament, when only a small amount of the medicament is charged, the rigidity of the sheet material surpasses the pressure generated due to self-weight of the medicament and the container cannot be inflated, as a result, the medicament is merely spread like a film between sheets over a wide area.

If a small-content medicament is spread over a wide area in this way, at the time of sealing the secondary medicament-housing chamber by heat sealing, the medicament itself comes into contact with the heat-sealing part to cause a problem such as sealing failure or deterioration of the medicament. In addition, a housing chamber with a large area is necessary for housing a small amount of a secondary medicament and an excessively large medical container results to incur a problem of bad usability.

As for the medical container in the case where the. inner content ratio among medicaments housed in respective medicament-housing chambers is large, JP-A-2002-165864 (the term "JP-A" as used herein means an "unexamined published Japanese patent application") describes a container in which a peelable weak seal is used for one partition of a housing container, a plurality of housing containers are joined through the weak seal part, and medicaments can be mixed on use. However, if a small-content secondary medicament chamber partitioned by a seal partition is formed in a medical container comprising a sheet material, a large area must be ensured for the secondary medicament chamber, as a result, the medical container as a whole becomes very large and its usability is bad.

JP-A-2003-159309 describes a container in which a relatively small secondary medicament-housing container part is formed by using a cylindrical injection molded member and can be joined with a primary medicament container part by the same technique as used for joining a cylindrical port for liquid discharge. However, in order to attain communication between the secondary medicament-housing chamber formed by using an injection molded member and the primary medicament chamber, a part of the injection molded member dividing these two chambers must be fractured to remove the partition, and the force for this communication operation must be suppressed to such an extent of allowing for almost no generation of fine pieces, particles or the like or not disturbing the transfusion. Therefore, the design and production of the injection molded member and the management of production become very difficult.

Furthermore, in the case where two or more secondary medicaments are used and these medicaments cannot be mixed in advance during storage but must be mixed on use, secondary medicament-housing container parts prepared as many as the number of secondary medicaments by using the injection molded member must be joined to the primary medicament container part and this is cumbersome from the mechanical point of view and the workability point of view.

JP-A-2003-62038 describes a case where since the secondary medicament-housing container part becomes relatively large when a flat bag formed of a sheet is used, a bag-shaped secondary medicament-housing container part is housed in a primary medicament container so as to suppress increase in the size of the entire medicament. In order to accommodate a secondary medicament-housing container part in a primary medicament container, foreign matters attached to the surface of the secondary medicament-housing container part must be thoroughly removed and the secondary medicament-housing container must be inserted by opening the primary medicament container in a clean environment, but this is very cumbersome from the mechanical point of view and the workability point of view.

Furthermore, JP-A-2000-5275 discloses a medical container in which a container for housing a relatively small-content secondary medicament is formed to intrude into a suspension hole. The object of this invention is to greatly reduce a danger of forgetting the operation of adding a small-content secondary medicament by passing the secondary medicament through the partition between the secondary medicament-housing chamber and the primary medicament-housing chamber. More specifically, on hanging a transfusion container, a notice is directed to the secondary medicament due to disturbance of the secondary medicament chamber intruded into the suspension hole, and a failure of forgetting to mix the medicament is thereby prevented. It is stated that for the purpose of distinguishing whether the secondary medicament is mixed or not, the material constituting the small-content secondary medicament chamber preferably has flexibility.

It is also stated that when the secondary medicament is not mixed and remains in the secondary medicament chamber, the mixing medicament chamber is inflated and therefore, this can be easily viewed from outside. As understood from these, in the invention described in JP-A-2000-5275, the material constituting the secondary medicament-housing chamber is substantially soft and the secondary medicament-housing chamber is inflated when housing a secondary medicament but is deflated when the secondary medicament is mixed with the primary medicament. Such a secondary medicament-housing container part comprising a substantially soft material and being deflated in the state of not housing a secondary medicament requires a large area for housing a small-content secondary medicament, and a very large medical container results.

As described above, the invention of JP-A-2002-165864 has a problem that when a container for housing a small-content secondary medicament is produced from a planar container capable of weak sealing, a container with a large area is necessary and the size of the entire medicament becomes large. In the invention of JP-A-2003-159309, when an injection molded member is used for the secondary medicament-housing container part, opening to the primary medicament container can be attained by fracturing a part of the injection molded member at the mixing on use. Therefore, the injection molded member must be designed and produced not to generate fine pieces, particles or the like at the fracturing and the management of production is very severe.

In the invention of JP-A-2003-62038, in order to accommodate a secondary medicament-housing container part in a primary medicament container, foreign matters attached to the surface of the secondary medicament-housing container part must be thoroughly removed and an operation of opening the primary medicament container in a clean environment and placing and fixing the secondary medicament-housing container part therein must be performed. Such a process requires a mechanically complicated apparatus and moreover, the apparatus must be installed and operated in a clean environment. Furthermore, there is a problem that the control for preventing foreign matters from mingling is very cumbersome.

In the invention of JP-A-2000-5275, if the container for housing a small-content secondary medicament is produced in a shape capable of weak sealing, a container with a large area is necessary and the entire medicament size becomes large. In this patent publication, it is also disclosed to use the injection molded member for the partition wall dividing a mixing medicament container and a primary medicament container or for the mixing medicament container itself, but in such a case, there arises a problem that the production process is more cumbersome and difficult than in the case of using the peelable partitioning means and the produced container becomes expensive.

The present invention has been made under these circumstances and an object of the present invention is to provide a relatively compact medical liquid container which is free from sealing failure in the seal portion at the peripheral edge of the liquid medicament-housing chamber and also free from deterioration of a medicament housed in a small amount and ensures good usability as a medical container; and a preparation-containing medical liquid container.

DISCLOSURE OF THE INVENTION

In order to attain the above-described object, the present invention provides a medical liquid container having a primary liquid medicament-housing chamber for housing a medicament and at least one secondary liquid medicament-housing chamber for housing a liquid medicament smaller in the amount than the liquid medicament housed in the primary liquid medicament-housing chamber, which is connected with the primary liquid medicament-housing chamber, an inside of the primary liquid medicament-housing chamber and an inside of the secondary liquid medicament-housing chamber being communicatably divided, wherein the secondary liquid medicament-housing chamber has a bulge part bulged such that the internal medicament-housing space before housing a medicament is larger than the volume of the housed medicament.

In the medical liquid container, it is preferable that the secondary liquid medicament-housing chamber be liquidtightly sealed, and communicatably divided from the primary liquid medicament-housing chamber. In this case, it is also preferable that the liquidtight seal is formed at the outside of the primary liquid medicament-housing chamber.

In the medical liquid container, it is preferable that the primary liquid medicament-housing chamber be made of a flexible sheet material.

The bulge part may comprise two sheet members and a separation member separating those two sheet members from each other to form a space and being housed in the secondary liquid medicament-housing chamber. The bulge part may be formed by cold stretching or heat stretching of a sheet member. Also, the secondary liquid medicament-housing chamber may be a blow-molded article.

The primary liquid medicament-housing chamber may comprise a plurality of housing chambers divided by a peelable liquidtight seal. A preparation-containing medical liquid container housing a medicament in each of the primary liquid medicament-housing chamber and the secondary liquid medicament-housing chamber of the above-described medical liquid container is provided. The secondary liquid medicament-housing chamber may be a preparation-containing secondary liquid medicament-housing chamber produced by a method of continuously performing formation of a chamber by blow molding, housing of a medicament and sealing of the chamber.

In the preparation-containing medical liquid container, it is preferable that a medicament containing any one or more of a sugar, an electrolyte, and an amino acid be housed in the primary liquid medicament-housing chamber. Simultaneously, it is preferably that a medicament containing any one or more of a water-soluble vitamin, a fat-soluble vitamin and a trace element be housed in the secondary liquid medicament-housing chamber.

According to the present invention, a bulge part larger, before housing a medicament, than the volume of a medicament housed in the internal medicament-housing space is previously formed in the secondary liquid medicament-housing chamber, whereby the medicament is prevented from spreading like a film between sheets over a wide area but housed with a thickness in the bulge part. By feeding a small-content medicament into this bulge part, contact of the medicament itself with the heat-seal part and occurrence of sealing failure can be prevented at the time of sealing the secondary liquid medicament-housing chamber by heat sealing. Furthermore, the medicament is also prevented from deterioration due to contact with the heat seal and a medicament in a good state is housed in the bulge part. In addition, the area of the secondary liquid medicament-housing container can be made small and a medical liquid container with compactness in its entirety and good usability can be obtained.

BEST MODE FOR CARRYING OUT THE INVENTION

Figure 1:
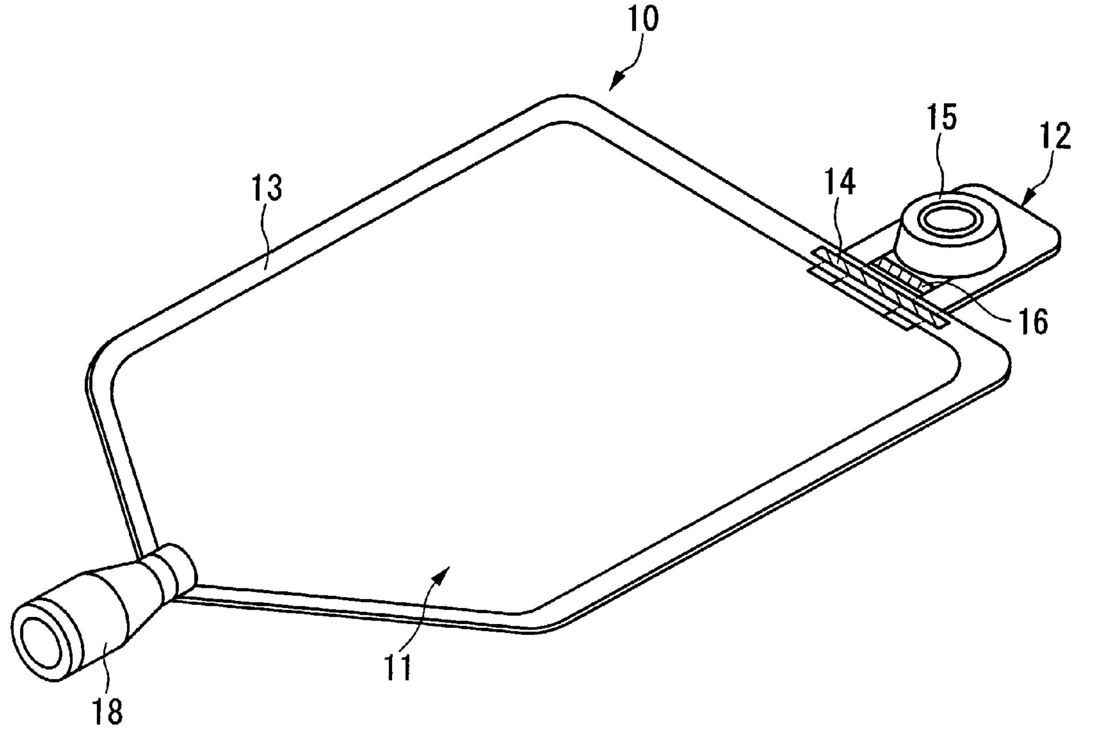
FIG. 1 is a perspective view showing an embodiment of the medical liquid container of the present invention.

The present invention is described in detail below by referring to the drawings. FIG. 1 is an outer appearance perspective view showing one example of the medical liquid container of the present invention. The medical liquid container 10 comprises a primary liquid medicament-housing chamber 11 for housing a first liquid medicament and a secondary liquid medicament-housing chamber 12 for housing a second liquid medicament smaller in the amount than the first liquid medicament housed in the primary liquid medicament-housing chamber 11, which is connected with the primary liquid medicament-housing chamber 11.

In the primary liquid medicament-housing chamber 11, almost the entire circumference of the peripheral edge part forms an unseparably sealed strong seal part 13 and the entirety is formed from a sheet-like member having flexibility, such as synthetic resin film. The resin used for the synthetic resin film is not particularly limited as long as it is a resin used in the field of medical container. Specific examples thereof include a polyolefin resin, a polyamide resin, a polyester resin, a poly(meth)acrylate, a polyvinyl chloride, a polyvinylidene chloride, a polyethersulfone and an ethylene-vinyl alcohol copolymer. Among these, a polyolefin resin is preferred because this is inexpensive and excellent in the transparency, flexibility and hygiene.

Examples of the polyolefin resin include a polyethylene-based resin such as high-density polyethylene, medium-density polyethylene, high-pressure low-density polyethylene, linear low-density polyethylene and ethylene-vinyl acetate copolymer, an olefin-based elastomer such as ethylene-$\alpha$-olefin random copolymer, a polypropylene-based resin such as polypropylene, ethylene-propylene random copolymer and $\alpha$-olefin-propylene random copolymer, a cyclic polyolefin resin, and a mixture thereof. Such a resin may be partially crosslinked for the purpose of enhancing heat resistance or the like.

Also, this synthetic resin film may be a single-layer film comprising one of those resins or two or more thereof in blend or may be a multilayer film comprising two or more layers. Such a synthetic resin film may have a thickness of 50 to 1,000 μm, preferably on the order of 100 to 500 μm. The synthetic resin film may be either a cast film produced by T-die casting or a blown film produced by blown film fabrication.

A discharge port 18 is formed at one end of the primary liquid medicament-housing chamber 11. This discharge port 18 is a liquid outlet for taking out a mixed liquid medicament resulting from mixing of the first liquid medicament and the second liquid medicament and by connecting thereto exclusive discharge means such as adapter or needle, the mixed liquid medicament is taken out from the medical liquid container 10. The discharge port is sometimes used as an injection port for mixing and injecting another medicament to the mixed liquid medicament. In addition to the discharge port 18, one injection port or two ore more injection ports may be separately joined to the one end, the other end or the like of the primary liquid medicament-housing chamber. The discharge port 18 may be joined to the secondary liquid medicament-housing chamber.

Figure 2:
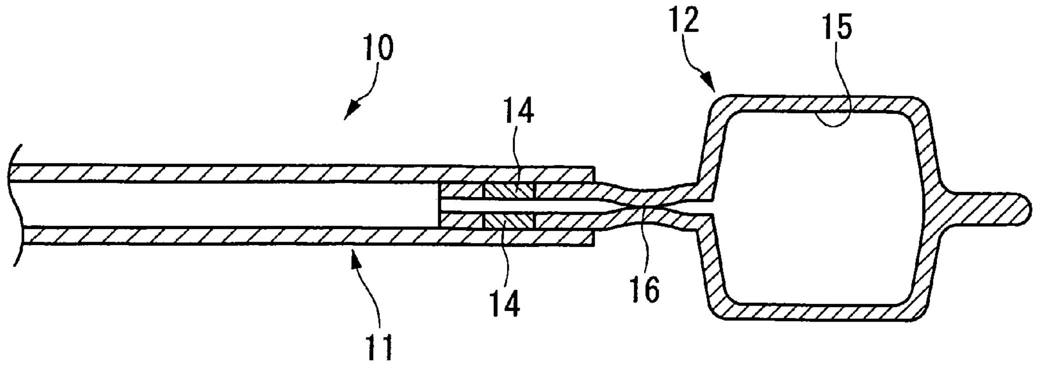
FIG. 2 is a principal part cross-sectional view of the medical liquid container shown in FIG. 1.

FIG. 2 is a principal part cross-sectional view showing a part of the primary liquid medicament-housing chamber 11, and a secondary liquid medicament-housing chamber 12. The secondary liquid medicament-housing chamber 12 is connected to the primary liquid medicament-housing chamber 11 at the opposite side to the side in which the discharge portion 18 is formed. In this embodiment, the primary liquid medicament-housing chamber 11 and the secondary liquid medicament-housing chamber 12 are formed separately, and they are overlapped at a connection part 14 and adhered such that they cannot peel each other. The secondary liquid medicament-housing chamber 12 has a bulge part 15 bulged such that the internal medicament-housing space before housing a secondary medicament is larger than the volume of the housed second medicament. The secondary liquid medicament-housing chamber 12 is formed stereoscopically.

The bulge part 15 may be formed stereoscopically, for example, by cold stretching or heat stretching of a sheet member or by blow molding using a die. The secondary liquid medicament-housing chamber 12 having such a bulge part 15 can be formed of various synthetic resins. Specific examples thereof include a polyolefin resin, a polyamide resin, a polyester resin, a poly(meth)acrylate, a polyvinyl chloride, a polyvinylidene chloride, a polyethersulfone and an ethylene-vinyl alcohol copolymer. Among these, a polyolefin resin is preferred because this resin is inexpensive and excellent in the transparency, flexibility and hygiene.

Examples of the polyolefin resin include a polyethylene-based resin such as high-density polyethylene, medium-density polyethylene, high-pressure low-density polyethylene, linear low-density polyethylene and ethylene-vinyl acetate copolymer, an olefin-based elastomer such as ethylene-α-olefin random copolymer, a polypropylene-based resin such as polypropylene, ethylene-propylene random copolymer and α-olefin-propylene random copolymer, a cyclic polyolefin resin, and a mixture thereof. Such a resin may be partially crosslinked for the purpose of enhancing heat resistance or the like. Furthermore, the secondary liquid medicament-housing chamber having a bulge part 15 may have a single-layer or multilayer structure comprising one or more resin selected from those various synthetic resins.

Particularly, in the case of a medicament which adsorbs to a polyethylene resin or a polypropylene resin generally employed for medical usage, such as fat-soluble vitamin compound, the secondary liquid medicament-housing chamber preferably takes a multilayer structure using a cyclic polyolefin for the innermost layer coming into contact with the medicament.

In the case where the secondary liquid medicament-housing chamber houses a medicament such as antibiotic which deteriorates due to oxygen or the like in the outer air, the secondary liquid medicament-housing chamber preferably takes a multilayer structure comprising a resin having a gas barrier property against oxygen or the like, such as ethylene-vinyl alcohol copolymer, and another resin. Furthermore, in order to elevate the adhesive strength between respective resin layers in the multilayer structure, a resin having compatibility in common may be mixed in one or both of the resins constituting the adjacent layers, or a layer comprising a resin having compatibility in common, for example, an adhesive resin such as ethylene-vinyl acetate copolymer, may be added between those layers.

In the case where a medicament which deteriorates due to light (e.g., ultraviolet ray), such as vitamin compound, is housed as the secondary liquid medicament, a layer of shielding light in the wavelength region harmful to the medicament may be added. For example, in order to shield ultraviolet ray, an iron oxide-containing polyolefin resin may be used for the outer layer of the secondary liquid medicament-housing chamber in a multilayer structure.

When the secondary liquid medicament-housing chamber has a multilayer structure, the multilayer structure may be formed by co-extrusion molding of multiple layers. Alternatively, single-layer or multilayer materials may be bonded by heat lamination, dry lamination or the like to obtain an objective multilayer structure.

The second medicament (secondary medicament) housed in the secondary liquid medicament-housing chamber 12 is mixed with the first medicament (primary medicament) housed in the primary liquid medicament-housing chamber 11 on use immediately before administering the medicament to a patient or the like. In order to facilitate the mixing on use, it is preferable that a liquidtight seal 16 allowing for communication between the inside of the secondary liquid medicament-housing chamber 12 and the inside of the primary liquid medicament-housing chamber 11 upon pressing the bulge part 15 of the secondary liquid medicament-housing chamber 12 or pressing the primary liquid medicament-housing chamber 11, be formed.

The liquidtight seal 16 is formed such that it communicatably divides the inside of the primary liquid medicament-housing chamber 11 and the inside of the secondary liquid medicament-housing chamber 12. The configuration of the liquidtight seal 16 is not limited, but it is preferable that the liquidtight seal 16 be formed so as to be peelable by heat-seal joining. In addition, as shown in FIG. 2, it is also preferable that the inside of the primary liquid medicament-housing chamber 11 and the inside of the secondary liquid medicament-housing chamber 12 be communicably divided by liquidtight seal 16 joining the secondary liquid medicament-housing chamber 12. When the medical liquid container has such structure, it is possible to house the second medicament in the secondary liquid medicament-housing chamber 12, and liquidtight seal 16 the secondary liquid medicament-housing chamber 12, and then connect the secondary liquid medicament-housing chamber 12 with the primary liquid medicament-housing chamber 11. Since the second medicament in the secondary liquid medicament-housing chamber 12 is not contacted with ambient air continuously, the medical liquid container having such a structure is preferable from the aspect of good hygiene.

Figure 3:
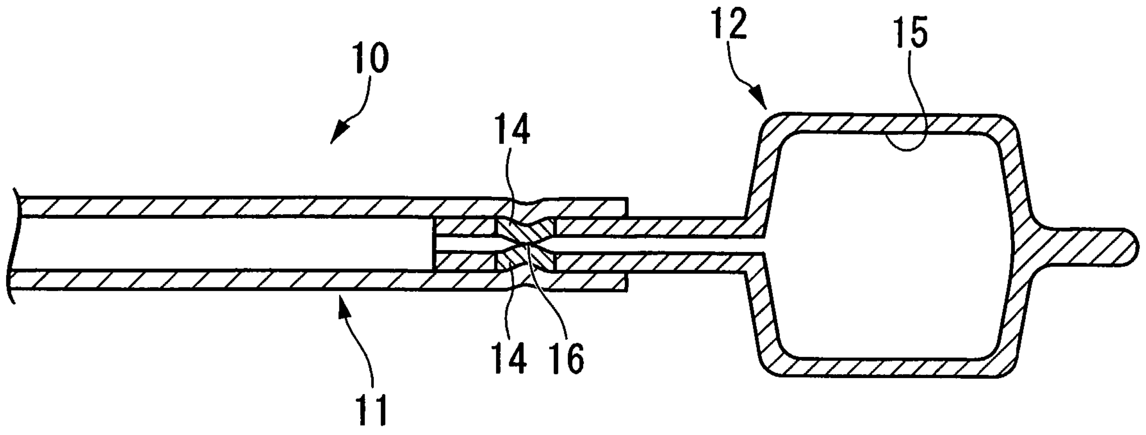
FIG. 3 is a principal part cross-sectional view of another embodiment of the medical liquid container of the present invention.
Figure 4A:
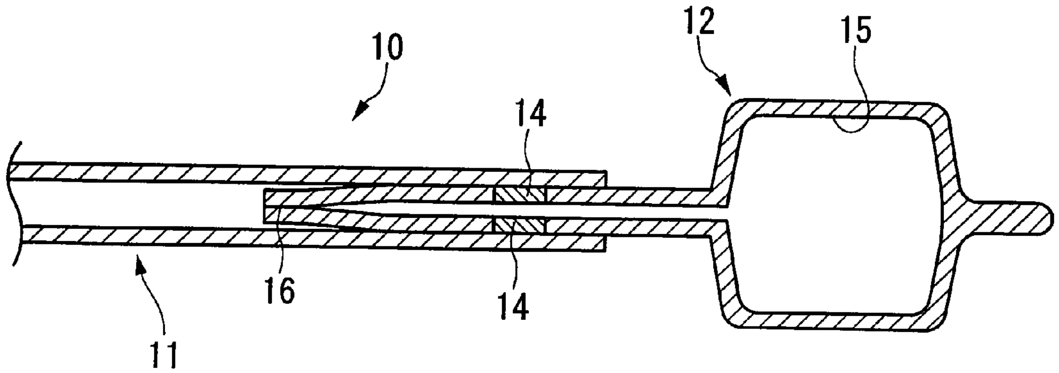
FIG. 4A is a principal part cross-sectional view of another embodiment of the medical liquid container of the present invention.

Specific embodiments of the position of the liquidtight seal 16 in the secondary liquid medicament-housing chamber 12 include an inside of the primary liquid medicament-housing chamber 11 as shown in FIGS. 3 and 4A, in addition to an outside of the primary liquid medicament-housing chamber 11 as shown in FIG. 2. In the embodiment shown in FIG. 3, the liquidtight seal 16 is formed so as to correspond to the connection part 14 in which the primary liquid medicament-housing chamber 11 and the secondary liquid medicament-housing chamber 12 are adhered. In the embodiment shown in FIG. 4A, the liquidtight seal 16 is formed at portion other than the connection part 14 in which the primary liquid medicament-housing chamber 11 and the secondary liquid medicament-housing chamber 12 are adhered. In this embodiment, the liquidtight seal 16 is formed at the edge portion of the secondary liquid medicament-housing chamber 12.

In any embodiments shown in FIGS. 2, 3, and 4A, it is possible to connect the primary liquid medicament-housing chamber 11 and the secondary liquid medicament-housing chamber 12 without subjecting the second medicament in the secondary liquid medicament-housing chamber 12 to ambient air, and these embodiments are excellent in hygiene. However, from the viewpoint of ease of peeling of the liquidtight seal 16 in using the medical liquid container, the embodiments shown in FIGS. 2 and 3 are preferable. Specifically, in the embodiments shown in FIGS. 2 and 3, it is possible to easily peel the liquidtight seal 16 by arbitrarily select and press the primary liquid medicament-housing chamber 11 or the secondary liquid medicament-housing chamber 12.

Figure 4B:
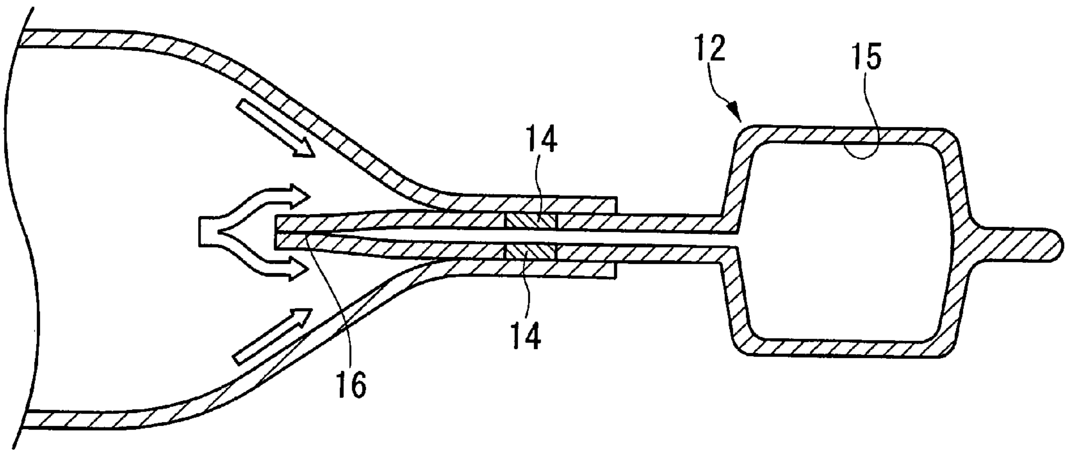
FIG. 4B is a view showing the medical liquid container show in FIG. 4A when the primary liquid medicament-housing chamber is pressed.

In contrast, in the embodiment shown in FIG. 4A, when the primary liquid medicament-housing chamber 11 is pressed, as shown in FIG. 4B, sufficient pressure to peel is not applied to the liquidtight seal 16. Due to this, it is necessary to press the secondary liquid medicament-housing chamber 12 to peel the liquidtight seal 16.

Therefore, from the viewpoint of ease of peeling of liquidtight seal 16 in using the medical liquid container, the embodiments shown in FIGS. 2 and 3 are preferable.

In addition, from the viewpoint of ease of production of the medical liquid container, the embodiment shown in FIG. 2 is more preferable than the embodiments shown in FIG. 3. Specifically, in the embodiment shown in FIG. 2, the liquidtight seal 16 is formed so as not to overlap the connection part 14 in which the primary liquid medicament-housing chamber 11 and the secondary liquid medicament-housing chamber 12 are adhered. There is technical difficulty to form the connection part 14 and the liquidtight seal 16 at the same position, which have different heat seal strengths. In addition, when the connection part 14 and the liquidtight seal 16, which have different heat seal strengths, are formed at the same position, thermal damage is applied to the same position at several time. However, in the embodiment in FIG. 2, since the liquidtight seal 16 of the secondary liquid medicament-housing chamber 12 is formed so as not to overlap the connection portion 14, these problems do not generate. Therefore, it is preferable that the liquidtight seal 16 of the secondary liquid medicament-housing chamber 12 be formed so as not to overlap the connection portion 14, and more preferable that the liquidtight seal 16 be formed at the outside the primary liquid medicament-housing chamber 11.

The liquidtight seal which can be peeled upon application of a pressure to allow for communication is not particularly limited in its formation method but may be formed, for example, by the method described in JP-A-2004-000476 where melt-bonding is performed such that the area occupied by the strong melt-bonding part in the melt-bonding part becomes less than 25%. Alternatively, the partition wall-forming portion of a blow molding die may be constituted to make the distance between opposing faces of the die to be broader than the distance undergoing complete melt-bonding or the distance completely not undergoing melt-bonding, so that the bonding can be suppressed to such an extent of allowing for communication while having satisfactory liquidtightness. Also, similarly to the above-described seal shape, the liquidtight seal can be formed by employing a die shape constituted such that the strong melt-bonding part occupies less than 25%.

The connection part 14 unseparably connecting the secondary liquid medicament-housing chamber 12 and the primary liquid medicament-housing chamber 11 can be formed by a technique such as heat-seal joining, joining through a cylindrical member, or joining through a partitioning member described in JP-A-2001-87350. Particularly, in the case of inserting the end part of the secondary liquid medicament-housing chamber 12 into the primary liquid medicament-housing chamber 11 and heat-sealing it to effect joining, when the sheet material constituting each chamber is made to have a multilayer structure and the resin of each layer is selected so that the sealing temperature at the joining of the outer face of the secondary liquid medicament-housing chamber 12 with the inner face of the primary liquid medicament-housing chamber 11 can be set to be lower than the temperature at the melt-bonding of inner faces of the secondary liquid medicament-housing chamber 12 with each other, the secondary liquid medicament-housing chamber 12 and the primary liquid medicament-housing chamber 11 can be joined by a simple and easy sealing process.

Inversely, in the case where the outer face of the primary liquid medicament-housing chamber 11 and the inner face of the secondary liquid medicament-housing chamber 12 are joined by heat sealing, when the sheet material constituting each chamber is made to have a multilayer structure and the resin of each layer is selected so that the sealing temperature at the joining of the outer face of the primary liquid medicament-housing chamber 11 with the inner face of the secondary liquid medicament-housing chamber 12 can be set to be lower than the temperature at the melt-bonding of inner faces of the primary liquid medicament-housing chamber 11 with each other, the secondary liquid medicament-housing chamber 12 and the primary liquid medicament-housing chamber 11 can also be joined by a simple and easy sealing process. In the examples of the present invention described by referring to FIGS. 2 to 4, a liquidtight seal 16 capable of being peeled to allow for communication is applied only to the secondary liquid medicament-housing chamber 12, but the liquidtight seal may be similarly applied to the primary liquid medicament-housing chamber 11 or may be applied both to the secondary liquid medicament-housing chamber 12 and the primary liquid medicament-housing chamber 11.

Figure 5:
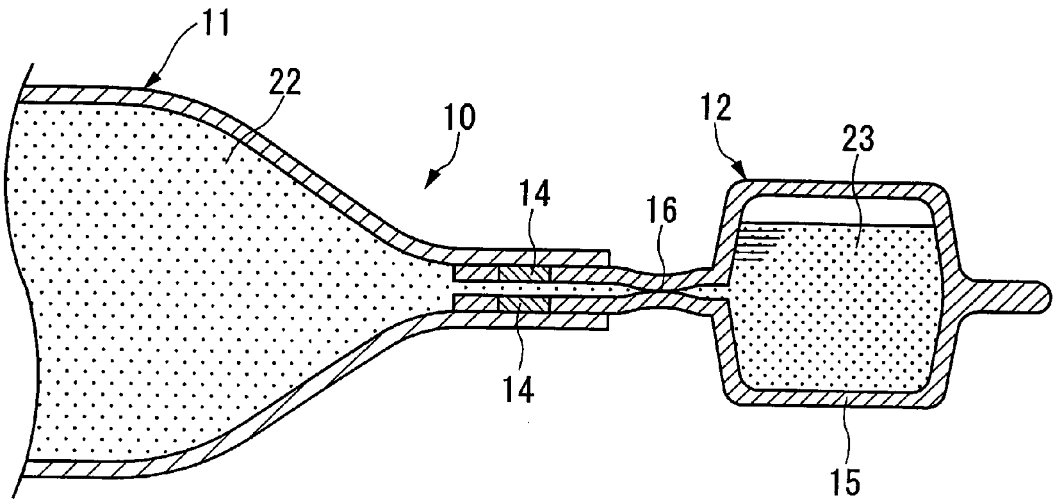
FIG. 5 is an explanatory view showing a mode of operation of the preparation-containing medical liquid container of the present invention.
Figure 6:
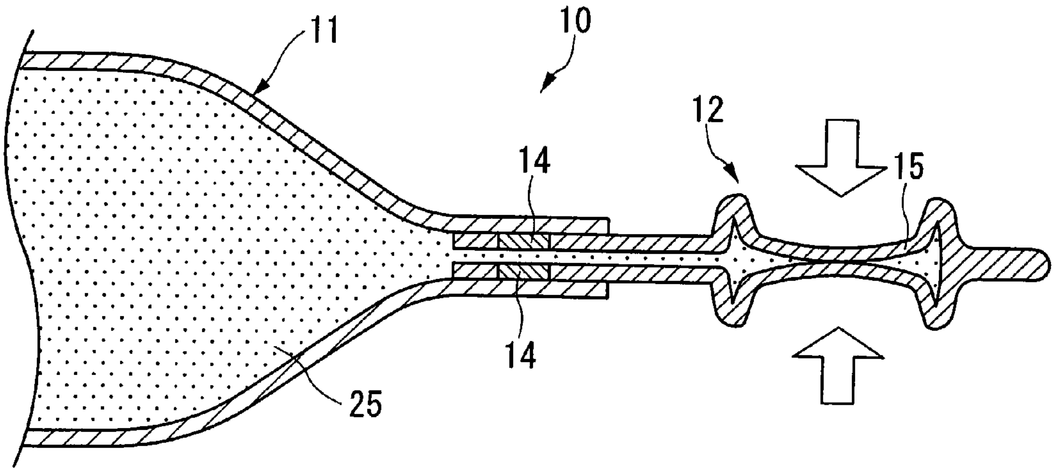
FIG. 6 is an explanatory view showing a mode of operation of the preparation-containing medical liquid container of the present invention.

The mode of operation of the preparation-containing medical liquid container obtained by housing medicaments in a medical liquid container having the above-described constitution is described by referring to FIGS. 5 and 6. As shown in FIG. 5, the preparation-containing medical liquid container 10 is housing, for example, approximately from 100 mL to 5 L of a medicament and a first medicament (primary medicament) 22 is housed in the primary liquid medicament-housing chamber 11, whereas a second medicament (secondary medicament) 23 with the content being equal to or smaller than the first medicament 22 is housed in the secondary liquid medicament-housing chamber 12. The secondary liquid medicament-housing chamber 22 is not particularly limited in its capacity but when the medicament content is small, the capacity is specifically 100 mL or less or depending on the case, as small as 10 mL or less.

At this time, a bulge part 15 having a volume larger than the second medicament 23 is previously formed in the secondary liquid medicament-housing chamber 12, whereby the medicament is prevented from spreading like a film between sheets over a wide area as compared with the case of feeding a small amount of a medicament into a secondary liquid medicament-housing chamber constituted by two flat sheet materials and can be housed with a thickness in the bulge part 15. By feeding a small amount of second medicament 23 into such a bulge part 15, contact of the second medicament 23 itself with the heat-seal part and occurrence of sealing failure can be prevented at the time of sealing the secondary liquid medicament-housing chamber 12 by heat sealing. Furthermore, the second medicament is also prevented from deterioration due to contact with the heat seal and a second medicament 23 in a good state is housed in the bulge part 15.

In using such a preparation-containing medical liquid container 10, as shown in FIG. 6, for example, the bulge part 15 of the secondary liquid medicament-housing chamber 12 is pressed and crushed, whereby the liquidtight seal 16 is peeled to allow for communication between the inside of the primary liquid medicament-housing chamber 11 and the inside of the secondary liquid medicament-housing chamber 12. As a result, the first medicament (primary medicament) 22 housed in the primary liquid medicament-housing chamber 11 and the second medicament (secondary medicament) 23 housed in the secondary liquid medicament-housing chamber 12 are mixed and a mixed medicament 25 is formed.

Figure 7:
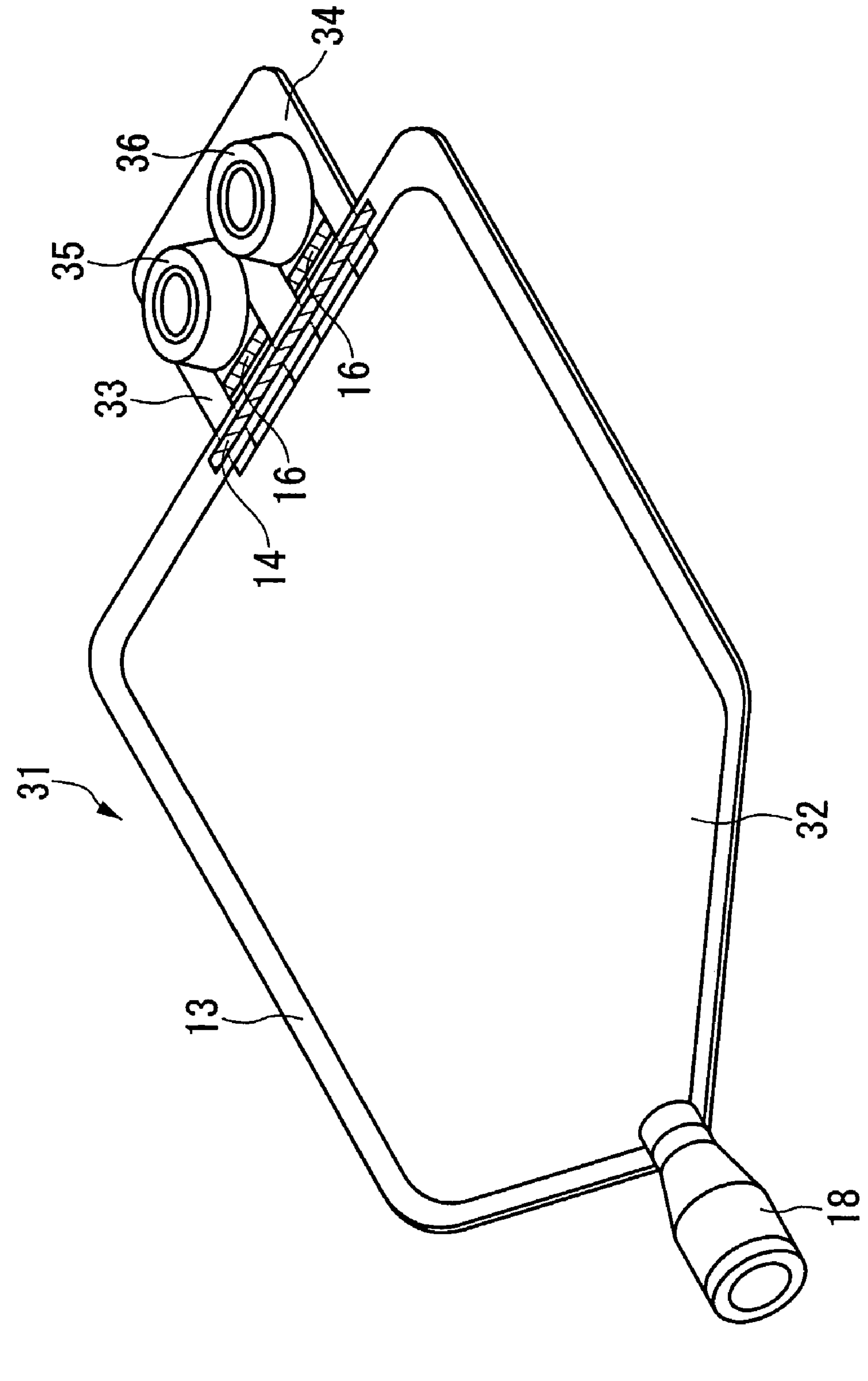
FIG. 7 is a perspective view showing another embodiment of the medical liquid container of the present invention.

Two or more secondary liquid medicament-housing chambers each having such a bulge part may be formed for one primary liquid medicament-housing chamber. As shown in FIG. 7, two secondary liquid medicament-housing chambers 33 and 34 are formed on one end side of the primary liquid medicament-housing chamber 32 of the medical liquid container 31. In these secondary liquid medicament-housing chambers 33 and 34, bulge parts 35 and 36 for housing a small amount of a liquid medicament while keeping the quality are formed, respectively.

In this way, by connecting two or more secondary liquid medicament-housing chambers 33 and 34 for one primary liquid medicament-housing chamber 32, a mixed liquid medicament in various combinations can be formed on use. Also, two secondary liquid medicament-housing chambers 33 and 34 shown in FIG. 7 are preferably molded and integrated at the same time. The integrated multiple secondary liquid medicament-housing chambers 33 and 34 can be joined with the primary liquid medicament-housing chamber 32 at one time and since the number of joining operations does not increase even if the number of secondary liquid medicament-housing chambers 33 is increased, the production of the medical liquid container is advantageously facilitated.

The preparation-containing medical liquid container described above may also employ a system such that the primary liquid medicament-housing chamber is pressed on use to apply a pressure to the primary liquid medicament and by the effect of this pressure, the liquidtight seal, which divides the primary liquid medicament-housing chamber and the secondary liquid medicament-housing chamber, is peeled to mix the primary liquid medicament and the secondary liquid medicament on use. Particularly, in the case where two or more secondary liquid medicament-housing chambers are joined, it is more easy and simple to press the primary liquid medicament-housing chamber and peel liquidtight seals all at once.

Figure 8:
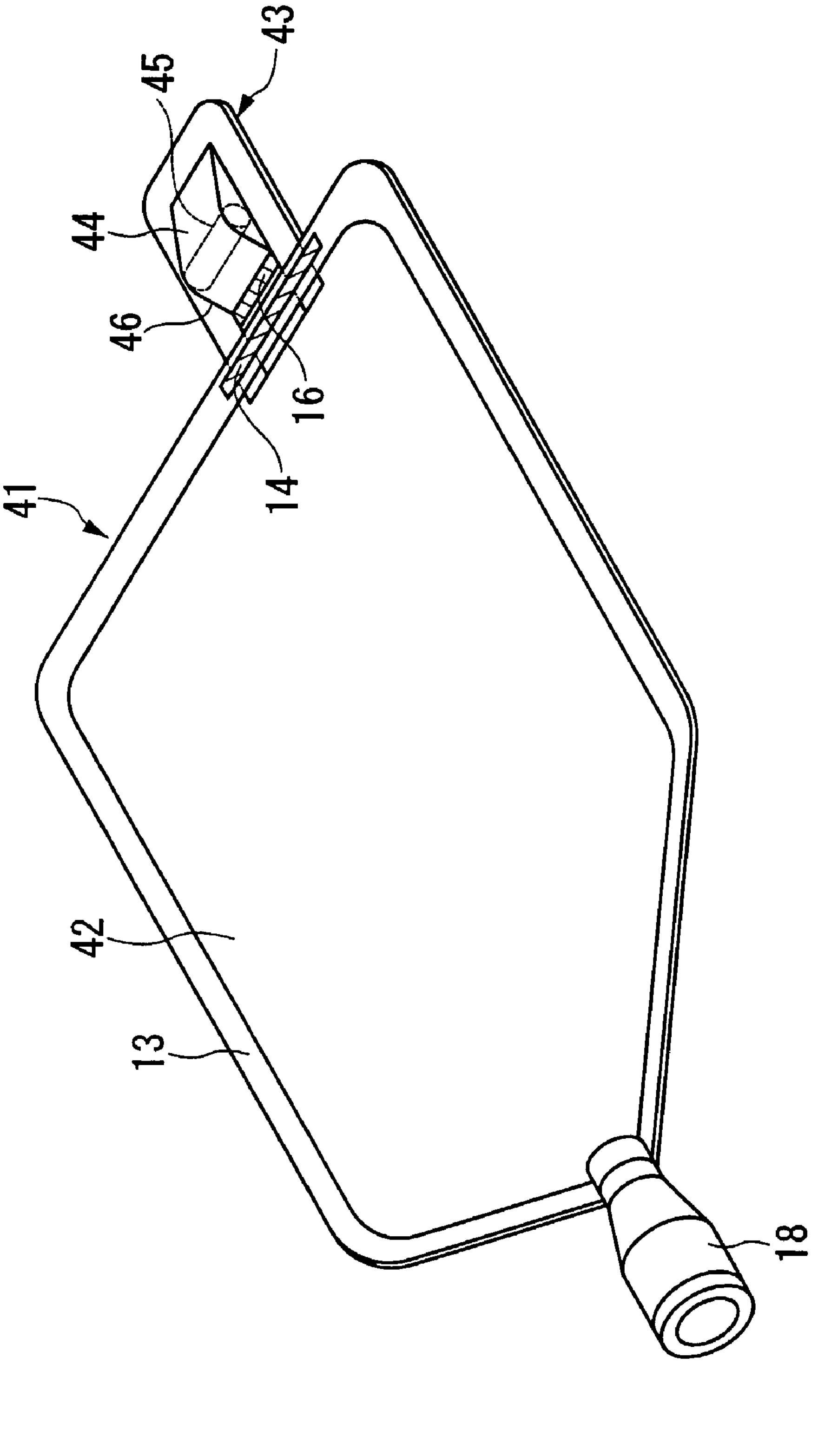
FIG. 8 is a perspective view showing another embodiment of the medical liquid container of the present invention.

FIG. 8 is another embodiment in which the constitution of the bulge part of the secondary liquid medicament-housing chamber is changed. In the secondary liquid medicament-housing chamber 43 connected to the primary liquid medicament-housing chamber 42 of the medical liquid container 41 of this embodiment, the bulge part 46 is formed by housing a separation member 45 between two sheet members 44.

This separation member 45 is not limited in its shape and as long as two sheet members 44 can be separated from each other to form a fixed space before housing a medicament, the separation member may have, for example, a spherical, columnar, cubic or rectangular parallelepiped shape other than the cylindrical shape shown in FIG. 8. As for the two sheet members, one sheet member may be folded or a blown film may be used. The separation member 45 may be formed of, for example, a polyolefin resin such as polyethylene resin, polypropylene resin and cyclic polyolefin resin, a polyamide resin, a polyester resin, a poly(meth)acrylate, a polyvinyl chloride, a polyvinylidene chloride, a polyethersulfone, an ethylene-vinyl alcohol copolymer or a blend thereof.

Figure 9:
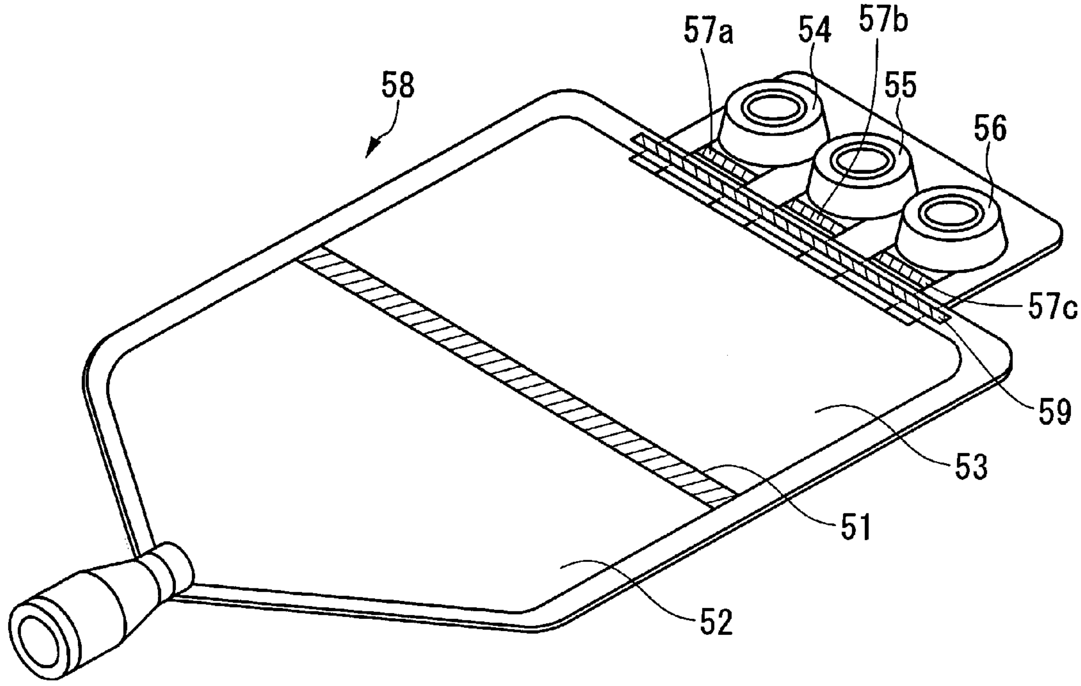
FIG. 9 is a perspective view showing another embodiment of the medical liquid container of the present invention.

Furthermore, in the medical liquid container, the primary liquid medicament-housing chamber may be divided into a plurality of chambers by communicatable liquidtight seal. For example, as shown in FIG. 9, the medical liquid container 58 may comprise first and second primary liquid medicament-housing chambers 52 and 53, of which the insides are divided by a peelable liquidtight seal 51, and three secondary liquid medicament-housing chambers 54, 55 and 56 connected to the second primary liquid medicament-housing chamber 53 by the connection part 59. In this medical liquid container 58, two kinds of primary liquid medicaments and three kinds of secondary liquid medicaments can be mixed on use. Also, an injection port for co-injecting a medicament may be fixed to the second primary liquid medicament-housing chamber 53.

In the medical liquid container 58 in this embodiment, only the secondary liquid medicament-housing chambers 54, 55 and 56 are provided with the liquidtight seals 57*a*, 57*b*, and 57*c*, and these liquidtight seals 57*a*, 57*b*, and 57*c* are positioned at the outside of the second primary liquid medicament-housing chamber 53. Due to this structure, it is possible to seal the secondary liquid medicament-housing chambers 54, 55 and 56 with the liquidtight seals 57*a*, 57*b*, and 57*c*, and then connect the secondary liquid medicament-housing chambers 54, 55 and 56 with second primary liquid medicament-housing chamber 53, and this is excellent in hygiene. In addition, it is possible to peel simultaneously the liquidtight seal 51, which divides the inside of the first primary liquid medicament-housing chamber 52 and the inside of the second primary liquid medicament-housing chamber 53, and all of the liquid seals 57*a*, 57*b*, and 57*c*, which divide the inside of the second primary liquid medicament-housing chamber 53 and the insides of the secondary liquid medicament-housing chambers 54, 55 and 56 by only one operation of pressing the second primary liquid medicament-housing chamber 53 connected to the secondary liquid medicament-housing chambers 54, 55 and 56. According to such a medical liquid container 58, it is not necessary to complicated operations such as peeling all of the liquid seals 51, 57*a*, 57*b*, and 57*c* in turn, and preparation of a medicament is easy, and it is possible to prevent a generation of a trouble such as a failure of forgetting to peel one of three liquidtight seals 57*a*, 57*b*, and 57*c*.

The medical liquid container of the present invention can be used, for example, as a container for housing a kit preparation for intravenous hyperalimentation or a kit preparation for peripheral parenteral nutrition, which are used in the intravenous hyperalimentation method, or for housing a component nutrition used in the enteral nutrition method. The preparation-containing medical liquid container of the present invention is the medical liquid container of the present invention in which a medicament is housed in each of the primary liquid medicament-housing chamber and the secondary liquid medicament-housing chamber. The primary medicament housed in the primary liquid medicament-housing chamber is not particularly limited, but examples thereof include a solution such as distilled water, an electrolyte infusion such as physiological saline, a saccharides infusion such as glucose solution, an amino acid infusion such as amino acid preparation, and a fat infusion such as fat emulsion.

In the case where the primary liquid medicament-housing chamber comprises a plurality of chambers, the primary medicament is not particularly limited, but examples thereof include a nutrient infusion containing any one or more of sugar, electrolyte, amino acid, fat emulsion and the like, a blood substitute infusion comprising a combination of various electrolytes, and a dialysis fluid comprising a combination of sugar and electrolyte. The secondary medicament housed in the secondary liquid medicament-housing chamber is also not particularly limited, but examples thereof include vitamins (e.g., water-soluble vitamin, fat-soluble vitamin), trace metal (e.g., copper, iron, manganese, zinc), iodine, calcium chloride for correction, insulin, antibiotic, anticancer drug, anti-peptic ulcer agent, hepatic disorder remedy, cardiac, analgesic, antipyretic analgesic, anesthetic, fat emulsion, hypotensive agent, vasodilator, hormone preparation and heparin. The medicament housed is not limited to a liquid medicament but may be a solid or powder medicament.

Particularly, in the case of housing a liquid medicament in the secondary liquid medicament-housing chamber, a preparation-containing secondary liquid medicament-housing chamber produced by a method of continuously performing formation of a chamber by blow molding, housing of a medicament and sealing of the chamber is preferably used, because the medicament can be sterilely housed in the secondary liquid medicament-housing chamber without opening the secondary liquid medicament-housing chamber.

Examples of the kit preparation for intravenous hyperalimentation used in the intravenous hyperalimentation method, which is housed in the preparation-containing medical liquid container of the present invention, include a high calorie infusion used as an initiating solution or a maintenance solution. In a preferred embodiment of the high calorie infusion, a medicament containing any one or more of sugar, electrolyte and amino acid is housed in the primary liquid medicament-housing chamber, and a medicament containing any one or more of water-soluble vitamin, fat-soluble vitamin and trace element is housed in the secondary liquid medicament-housing chamber.

INDUSTRIAL APPLICABILITY

According to the present invention, a bulge part larger, before housing a medicament, than the volume of a medicament housed in the internal medicament-housing space is previously formed in the secondary liquid medicament-housing chamber, whereby the medicament is prevented from spreading like a film between sheets over a wide area but housed with a thickness in the bulge part. By feeding a small amount of medicament into this bulge part, contact of the medicament itself with the heat-seal part and occurrence of sealing failure can be prevented at the time of sealing the secondary liquid medicament-housing chamber by heat sealing. Furthermore, the medicament is also prevented from deterioration due to contact with the heat seal and a medicament in a good state is housed in the bulge part. In addition, the area of the secondary liquid medicament-housing container can be made small and a medical liquid container with compactness in its entirety and good usability can be obtained.

The invention claimed is:

1. A medical liquid container having a primary liquid medicament-housing chamber for housing a medicament and at least one secondary liquid medicament-housing chamber for housing a liquid medicament smaller in the amount than the liquid medicament housed in the primary liquid medicament-housing chamber, which is connected to the primary liquid medicament-housing chamber, an inside of the primary liquid medicament-housing chamber and an inside of the secondary liquid medicament-housing chamber being communicatably divided, wherein said secondary liquid medicament-housing chamber has a bulge part bulged such that the internal medicament-housing space before housing a medicament is larger than the volume of the housed medicament, the secondary liquid medicament-housing chamber is liquid tightly sealed, and communicatably divided from the primary liquid medicament-housing chamber, the liquidtight seal is formed at the outside of the primary liquid medicament-housing chamber, the end part of the secondary liquid medicament-housing chamber is inserted into the primary liquid medicament-housing chamber and heat-sealed, and the primary and secondary liquid medicament-housing chambers are made of a sheet material having a multilayer structure in which a heat sealing temperature at a joining of the outer face of the secondary liquid medicament-housing chamber with the inner face of the primary liquid medicament-housing chamber is lower than a melt-bonding temperature of inner faces of the secondary liquid medicament-housing chamber with each other.

2. The medical liquid container as claimed in claim 1, wherein the primary liquid medicament-housing chamber is formed by a flexible sheet material.

3. The medical liquid container as claimed in claim 1, wherein said bulge part comprises two sheet members and a separation member separating said two sheet members from each other to form a space and being housed in said secondary liquid medicament-housing chamber.

4. The medical liquid container as claimed in claim 1, wherein said bulge part is formed by cold stretching or heat stretching of a sheet member.

5. The medical liquid container as claimed in claim 1, wherein said secondary liquid medicament-housing chamber is a blow-molded article.

6. The medical liquid container as claimed in claim 1, wherein said primary liquid medicament-housing chamber comprises a plurality of housing chambers divided by a separable liquid tight seal.

7. A preparation-containing medical liquid container housing a medicament in the medical liquid container claimed in claim 1, wherein the medicament is housed in each of the primary liquid medicament-housing chamber and the secondary liquid medicament-housing chamber of the medical liquid container.

8. The preparation-containing medical liquid container as claimed in claim 7, wherein said secondary liquid medicament-housing chamber comprises a preparation-containing secondary liquid medicament-housing chamber produced by a method of continuously performing formation of a chamber by blow molding, housing of a medicament and sealing of the chamber.

9. The preparation-containing medical liquid container as claimed in claim 7, wherein a medicament containing any one or more of a sugar, an electrolyte and an amino acid is housed in the primary liquid medicament-housing chamber and a medicament containing any one or more of a water-soluble vitamin, a fat-soluble vitamin and a trace element is housed in the secondary liquid medicament-housing chamber.

10. The preparation-containing medical liquid container as claimed in claim 7, wherein a medicament containing at least one of a water-soluble vitamin, a fat-soluble vitamin, and a trace element is housed in the secondary liquid medicament-housing chamber.

* * * * *

UNITED STATES PATENT AND TRADEMARK OFFICE

CERTIFICATE OF CORRECTION

PATENT NO. : 7,789,852 B2
APPLICATION NO. : 11/791372
DATED : September 7, 2010
INVENTOR(S) : Katsuyuki Yoshikawa and Manabu Nakamura It is certified that error appears in the above-identified patent and that said Letters Patent is hereby corrected as shown below:

Insert the following on the title page:

--Related U.S. Application Data
(60) Provisional application No. 60/632,951, filed on Dec. 6, 2004.--

Signed and Sealed this
Eighth Day of March, 2011

David J. Kappos
*Director of the United States Patent and Trademark Office*